US007265095B1

(12) United States Patent
Secombes et al.

(10) Patent No.: US 7,265,095 B1
(45) Date of Patent: Sep. 4, 2007

(54) MONOCLONAL ANTIBODY 3F1H10 NEUTRALISING VHSV (VIRAL HAEMORRHAGIC SEPTICAEMIA VIRUS)

(75) Inventors: Christopher John Secombes, Balmedie (GB); Charles Cunningham, Bergen (GB); Niels Lorenzen, Hundslund (DK)

(73) Assignees: Aberdeen University, Aberdeen (GB); Dianova, Arhus (DK)

( * ) Notice: Subject to any disclaimer, the term of this patent is extended or adjusted under 35 U.S.C. 154(b) by 0 days.

(21) Appl. No.: 10/088,780

(22) PCT Filed: Sep. 20, 2000

(86) PCT No.: PCT/GB00/03605

§ 371 (c)(1),
(2), (4) Date: Jul. 22, 2002

(87) PCT Pub. No.: WO01/21800

PCT Pub. Date: Mar. 29, 2001

(30) Foreign Application Priority Data

Sep. 20, 1999 (DK) ................ 1999 01329

(51) Int. Cl.
*A01N 43/04* (2006.01)
*A61K 31/70* (2006.01)
*A01N 63/00* (2006.01)
*A01N 65/00* (2006.01)
*C07K 17/00* (2006.01)

(52) U.S. Cl. ............ 514/44; 424/93.1; 530/387.1
(58) Field of Classification Search .......... 536/23.1, 536/23.53, 24.2; 514/44; 424/93.1
See application file for complete search history.

(56) References Cited

U.S. PATENT DOCUMENTS 5,543,144 A * 8/1996 Chang .............. 424/133.1
5,614,611 A    3/1997 Chang .............. 530/387.3

FOREIGN PATENT DOCUMENTS

WO    WO-96/37234 A1 * 11/1996 .......... 514/44
WO    WO99/25826         5/1999

OTHER PUBLICATIONS

Deonarain (1998) Exp. Opin. Ther. Pat., 8(1): 53-69.*
Gorecki (2001) Exp. Opin. Emerging Drugs, 6(2): 187-98.*
Verma, et al. (1997) Nature, 389: 239-42.*
Eck, et al. (1996) Goodman & Gilman's The Pharmacological Basis of Therapeutics, 9th Ed., McGraw-Hill, New York, NY., pp. 77-101.*
Marasco (2001) Curr. Topics Microbiol. Immunol., 260: 247-70.*
Daugherty (2000) Proc. Natl. Acad. Sci., USA, 97(5): 2029-34.*
Kalinke, et al. (1996) Eur. J. Immunol., 26: 2801-06.*
Cupit, et al. (2001) Virus Research, 81: 47-56.*
Bearzotti et al., "Fish Rhabdovirus Cell Entry Is Mediated by Fibronectin", J. Virology 1999 7703-7709.
Huang et al., "Mapping the neutralizing epitopes on the glycoprotein of infectious haematopoietic necrosis virus, a fish rhabdovirus", J. General Virology 1996 77:3303-3040.
Lorenzen et al., "Three monoclonal antibodies to the VHS virus glycoprotein:comparison of reactivity in relation to differences in immunoglobulin variable domain gene sequences", Fish & Shellfish Immunology 2000 10:129-142.
Nuñez et al., "Phospholipid Interactions of Peptide from the Fusion-Related Domain of the Glycoprotein of VHSV, a Fish Rhabdovirus", Virology 1998 243:322-330.
Prasad et al., "In vivo gene inoculation of a recombinant single-chain antitumor antibody induces anti-immunoglobin response", Cancer Gene Therapy, Jul.-Aug. 1997 4:253-259.

* cited by examiner

*Primary Examiner*—Joseph Woitach
*Assistant Examiner*—Robert M. Kelly
(74) *Attorney, Agent, or Firm*—Licata & Tyrrell P.C.

(57) ABSTRACT

The present invention relates to a non-infectious nucleic acid (RNA and DNA) construct constructed to express a recombinant antibody or antibody fragment in a host cell. The antibody molecule confers protection to the host against a pathogen, allergen or toxin. The host may be any animal including a human or a fish. More specifically, the antibody may be against viral haemorrhagic septicaemia virus.

3 Claims, 2 Drawing Sheets

Figure 1:
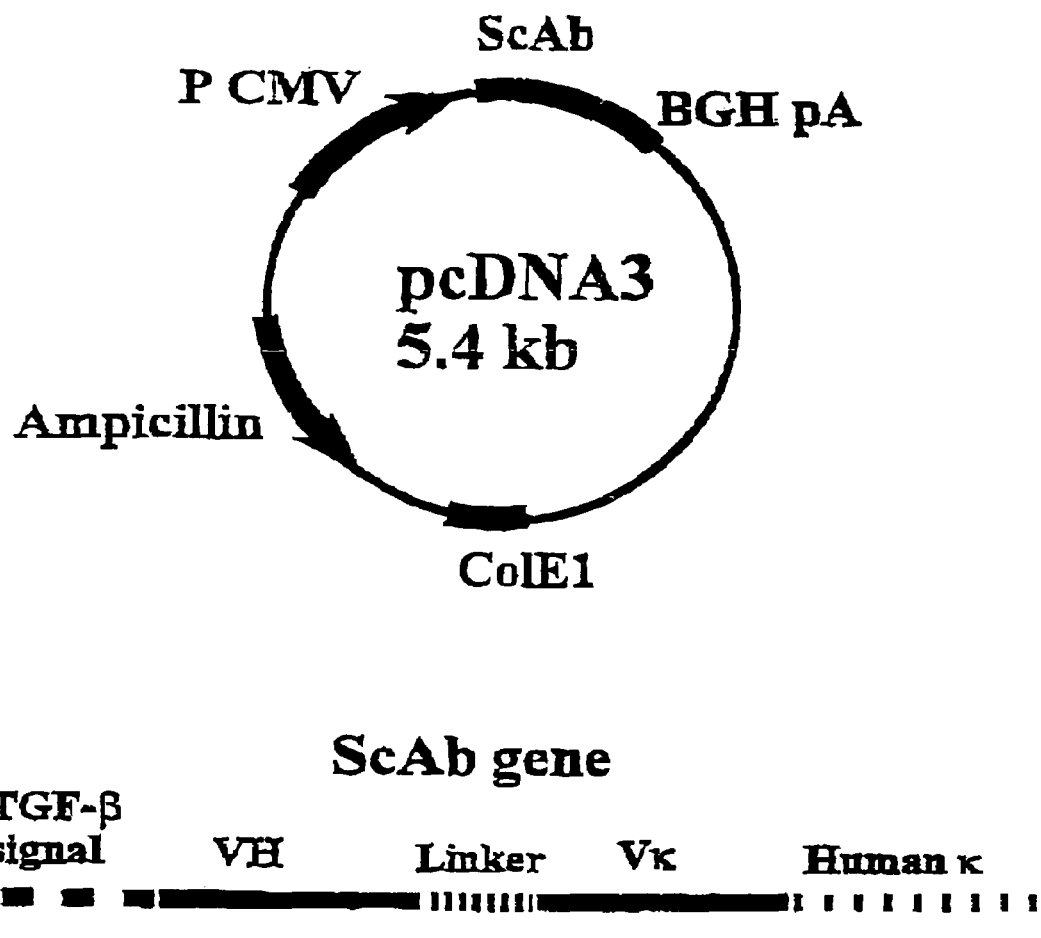

SEQUENCE LISTING

<160> NUMBER OF SEQ ID NOS: 1

<210> SEQ ID NO 1
<211> LENGTH: 1135
<212> TYPE: DNA
<213> ORGANISM: Artificial sequence
<220> FEATURE:
<223> OTHER INFORMATION: Synthetic

<400> SEQUENCE: 1

| | | | | | |
|---|---|---|---|---|---|
| cagtgtgcta | acatgagggc | agtgtgtttg | atgctgactg | ccttattgat | gctggaatat | 60 |
| gtgtgccgga | gtgaccaggt | gcagctgcag | gagtcaggac | ctggcctcgt | gaaaccttct | 120 |
| cagtctctgt | ctctcacctg | ctctgtcact | ggctactcca | tcaccagtgg | ttattactgg | 180 |
| acctggatcc | ggcagtttcc | aggaaataaa | ctggaatgga | tgggctacat | aagctacgac | 240 |
| ggtaccaata | actacaaccc | atctctcaca | aatcgaatct | ccatcactcg | tgacacatct | 300 |
| aagaaccagt | ttttcctgaa | gttgaaatct | gtgactactg | aggacacagc | tacatattac | 360 |
| tgtgtaagag | ggatctacta | tggtaacgac | tggtttgctt | actggggcca | agggaccacg | 420 |
| gtcaccgtct | cctcagaagg | caaatcttct | ggctctggct | ctgaatctaa | agtggatgac | 480 |
| atcgagctca | cccagtctcc | tgcctcccag | tctgcatctc | tgggagaaag | tgtcaccatc | 540 |
| acatgcctgg | caagtcagac | cattggtaca | tggttagcat | ggtatcaaca | gaaaccaggg | 600 |
| aaatctcctc | agctcctgat | ttatgctgca | accagtttgg | cagatggggt | cccatcaagg | 660 |
| ttcagtggta | gtggatctgg | cacaaaattt | tctttcaaga | tcagcagcct | acaggctgaa | 720 |
| gattttgtaa | gttattactg | tcaacaactt | tacagtactc | cgtacacgtt | cggaggggggg | 780 |
| accaagctcg | agatcaaacg | gactgtggct | gcaccatctg | tcttcatctt | cccgccatct | 840 |
| gatgagcagt | tgaaatctgg | aactgcctct | gttgtgtgcc | tgctgaataa | cttctatccc | 900 |
| agagaggcca | aagtacagtg | gaaggtggat | aacgccctcc | aatcgggtaa | ctcccaggag | 960 |
| agtgtcacag | agcaggacag | caaggacagc | acctacagcc | tcagcagcac | cctgacgctg | 1020 |
| agcaaagcag | actacgagaa | acacaaagtc | tacgcctgcg | aagtcaccca | tcagggcctg | 1080 |
| agttcgcccg | tcacaaagag | cttcaaccgc | ggagagtcat | aagttagata | tccat | 1135 |

MONOCLONAL ANTIBODY 3F1H10 NEUTRALISING VHSV (VIRAL HAEMORRHAGIC SEPTICAEMIA VIRUS)

This application is the U.S. National Stage of International Application No. PCT/GB00/03605, filed Sep. 20, 2000, which claims the benefit of priority to Danish Patent Application No. PA 1999 01329, filed Sep. 20, 1999.

The present invention relates to a non-infectious nucleic acid (RNA and DNA) construct constructed to express a recombinant antibody or antibody fragment in a host cell. The antibody molecule confers protection to the host against a pathogen, allergen or toxin. The host may be any animal including a human.

Passive immunization by injection of homologous or heterologous serum-antibodies is routinely used in humans for immunoprophylaxis of people traveling to foreign regions involving risk of exposure to exotic pathogens. In animals a similar strategy may be employed for protection of valuable specimens, but is generally too expensive for routine veterinary use. Passive immunisation of animals against infectious diseases is thus mostly done on an experimental basis with the aim of studying the function of structures such as antibodies in vivo and relating the results to in vitro experiments.

During the recent decade, diverse technologies for the in vitro production of antibodies by the use of recombinant DNA technology has been developed. The smallest functional recombinant antibody combining the actions of the heavy (H) and light (L) polypeptide chains as in the native molecule has proved to be the single chain variable-fragment construct (single chain FV). The single chain FV construct is composed of the variable parts of the H and L chains connected by a flexible spacer region. Such molecules have been used in various studies including virus neutralisation, cancer-immunotherapy and recently also in the form of DNA vaccines where plasmids encoding anti-idiotype single chain FV antibodies have proved able to induce an antigen-specific immune response. However, direct establishment of protective immunity to infectious diseases by prophylactic treatment with plasmid DNA carrying single chain FV genes encoding protective antibodies has not been described.

An object of the present invention is to provide a non-infectious nucleic acid construct which can produce an antibody molecule in vivo thereby conferring immunity to a disease.

A further object of the present invention is to provide a method of establishing immunity against a pathogen.

A yet further object of the present invention is to provide a method of therapy for animals which have deficient immune system.

An additional object of the present invention is to provide a method of therapy for an animal suffering from an allergic reaction or a method of preventing an allergic reaction.

For avoidance of doubt it should be noted that the word "animal" includes but is not restricted to mammals including humans.

According to an embodiment of the present invention there is provided a nucleic acid construct encoding a recombinant antibody molecule, said construct being adapted for the in vivo establishment of a protective immunity to an infectious disease in an animal.

According to a further embodiment of the present invention there is provided a nucleic acid construct encoding a recombinant antibody molecule, said construct is formulated for the in vivo prevention of an allergic reaction to an allergen in an animal.

According to a yet further embodiment of the present invention there is provided a nucleic acid construct encoding a recombinant antibody molecule, wherein said construct is formulated for the in vivo prevention of a reaction caused by the presence of a toxic substance in an animal.

The term recombinant antibody molecule encompasses a full size antibody, a single chain variable fragment or any part of an antibody which can recognise an antigen. In this connection, conveniently the antibody fragment does not have to be single chain. However, in some embodiments it is single chain.

It has now been found that the intramuscular injection of a nucleic acid construct, in the form of a plasmid, encoding a virus-neutralising single chain antibody fragment can mediate in vivo expression of antibodies which protect an animal against a possibly lethal exposure to a virus. This has been established in an experimental model which involves a fish rhabdovirus called viral haemorrhagic septicaemia virus (VHSV) in the rainbow trout (Oncorhynchus mykiss) as a host species.

According to a further embodiment of the present invention there is provided a nucleic acid construct, such as a plasmid, comprising an expression vector and a gene sequence for heavy and/or light chain variable domains of an antibody.

Preferably the heavy and light chain variable domains are linked by a linker sequence in order that they form what is known in the art as a single chain variable-fragment.

It is thought that the antibody fragment as expressed in and secreted from a host cell carrying the vector will act with the same specificity as a natural antibody would in the presence of a substance which it recongises. In this connection, for example, if the heavy and/or light chain variable domain were derived from a monoclonal antibody raised against dengue virus then if dengue virus infected a host who has received a nucleic construct expressing a single chain variable fragment produced from the heavy and light chain of the monoclonal antibody, the fragment would recognise cells infected with the dengue virus or the dengue virus particle itself and bind thereto thereby neutralising or inhibiting the virus and/or giving the host time to mount an immune response against the virus.

In preferred embodiments the expression vector is made for eukaryotic expression and/or is non infectious. For example, a bacterial plasmid, or a smaller DNA fragment carrying the variable fragment antibody gene within a eukaryotic expression operon including regulatory elements such as an enhancer, promoter and polyadenylation signal could be used. Alternatively, stabilised messenger RNA including a positive strand transcript of the variable-fragment antibody gene with translation signals may be employed.

The antibody fragment genes can be cloned by any method known to those skilled in the art, for example from hybridoma cells or directly from B-lymphocytes from immunized individuals. Nucleic acid constructs encoding protective antibody fragments can be prepared against any important pathogen/disease causing agent in animals including pathogens against which vaccines are not available or have proved insufficient. Furthermore, as a result of veterinary regulations, use of live vaccines may not be allowed. In such cases an alternative prophylactic measure would have to be taken. Such a measure could be the administration of the nucleic acid construct of the present invention. A list of possible pathogens is given below; this list is not intended to be exhaustive.

Viral haemorrhagic septicameia virus (fish)
Infectious haematopoietic necrosis virus (fish)
Infectious salmon anemia virus (fish)
Infectious pancreatic necrosis virus (fish)
Nodaviruses (fish)
Renibacterium salmoniarum (fish)
Pasteurella (fish)
Ichthyopthtirius mulitifiliis (fish)
NewCastle disease virus (fowl)
Infectious bursal disease virus (fowl)
Bovine respiratory syncytial virus (cattle)
Bovine virus diarrhoea virus (cattle)
Porcine reproductive and respiratory syndrome virus (pigs)
Pseudorabiesvirus (pigs)
Equine herpes virus 1 (horses)
Plasmocytosis virus (mink)
Rabies virus (dogs)
Feline leukemia virus (cats)
Foot and mouth disease (cattle)
Human immune deficiency virus (human)
Hepatitis A virus (human)
*Borrelia* sp. (human)
*Plasmodium* sp. (human)
Rabies virus (human)
Epstein-Barr virus (human)

In case of humans with either a congenital or acquired immunodeficiency, vaccines will generally be insufficient. In such cases, administration of a number of nucleic acid constructs according to the present invention encoding antibodies against a broad spectrum of pathogens may be considered.

For the purpose of prevention of allergic relations induced by IgE response, administration of nucleic acid constructs mediating expression of an allergen-specific recombinant antibody may be used to competitively inhibit binding of the allergen to the IgE molecules in the host. Alternatively gene constructs encoding anti-IgE antibodies may be used to interface with the interaction between IgE and mast cells in the allergic individual.

Administration of antibody gene constructs encoding antibodies to toxins or venoms can be used for the prophylactic treatment of individuals periodically being in high risk of exposure to toxic organisms. The venoms could, for example, be from snakes or spiders.

Conveniently the construct further comprises a gene encoding a signal sequence for the secretion of the product encoded by the gene sequence. The single sequence will allow the product of the gene sequence to be secreted from a cell in which the gene has been expressed, into the blood so that the product of the gene sequence can circulate therein. For example, the genes for the signal sequence of either rainbow trout transforming growth factor beta (TGF-beta), or murine Ig kappa-chain can be added to the 5' end of a gene to be administered to the fish. Other secretion signals, preferably of homologous origin to the host species may be employed. Examples of genes which encode proteins which act as secretion signals include the gene for immunoglobulin heavy and light chain secretion signals or other glycoprotein secretion signals. Preferably, the secretion signal should include a proteolytic cleavage site ensuring removal of the signal peptide before secretion of the antibody fragment.

Preferably the construct further comprises a known gene sequence which encodes a short peptide sequence that can be used to identify transfected cells. Such a gene sequence can be attached to the 3' end of the gene. Examples of such a sequence include a human kappa light chain construct or sequence encoding a six histidine residue. In both cases, an antibody specifically recognising the expressed peptide is commercially available.

The construct according to the present invention may be delivered by any suitable method, such as by injection (e.g intramuscularly), by a spray on a mucosa surface (e.g intranasally), by particle bombardment on skin/dermis through use of a gene gun, by electroporation or by uptake by an animal from an aqueous environment. In this connection, the plasmid may be encased in a liposome for administration to an animal. The construct may be administered to the animal topically, through inhalation or orally. For oral administration the construct should be protected from degradation by proper encapsulation.

It is preferred that in a composition or formulation for administration of the constructs there are present genes encoding the heavy and/or light chain variable fragments against several different epitopes or an variable fragment antibody gene expression library against a given pathogen. In this connection, the various fragments may be provided on one plasmid or they may be provided on several different gene constructs which are all present in the same formulation or other method of administration. In the alternative, each plasmid may have to be administered separately.

The invention also provides for a method for treating an animal, for example of mammal or a fish which comprises administering thereto a plasmid or other nucleic acid construct encoding a protective antibody fragment as previously described.

The invention thus provides for a method of therapy for an animal which has a deficient immune system.

The invention also provides for a therapeutic composition comprising the plasmid as previously described and a pharmaceutically acceptable diluent or carrier therefor. The composition may be formulated such that it is in the form of, for example, a vaccine, dosage form, cream, ointment, liquid or paint.

The invention will now be described by way of illustration only with reference to the following Example and Figures.

FIG. 1 shows a schematic drawing of the pCDNA3 plasmid with a single chain antibody (ScAb) gene construct inserted downstream of a strong eukaryotic promoter from cytomegalovirus (CMV). PCDNA3 is a commercially available eukaryotic expression vector (Invitrogen).

Figure 2:
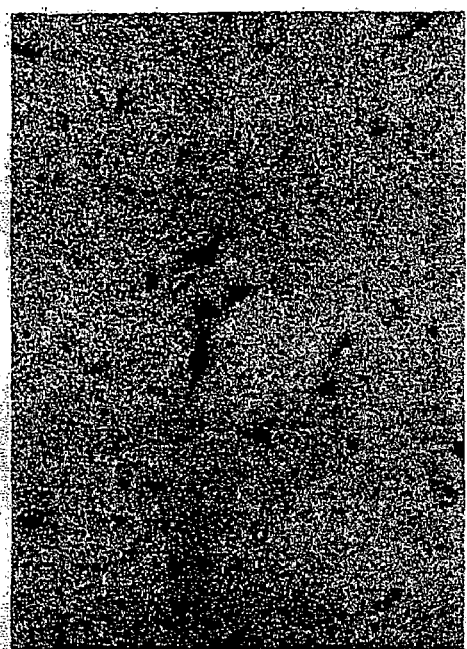
Figure 3:
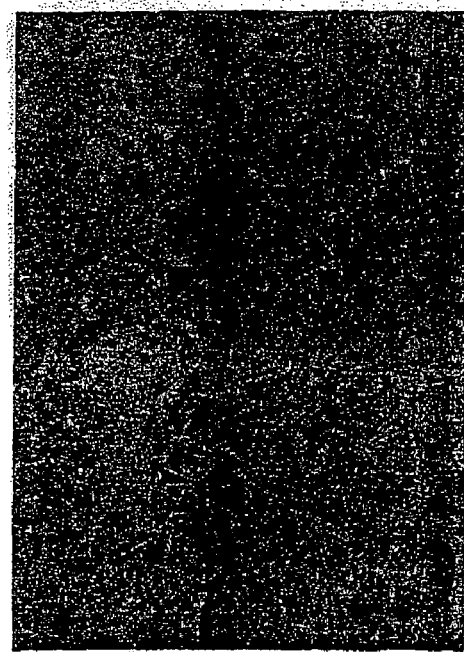

FIG. 2 shows a culture of EPC cells (passaged fish cells) transfected with a pCDNA3-BU1. BU1 is a ScAb gene construct encoding a recombinant antibody which is able to neutralise the fish pathogenic rhabdovirus, VHSV. BU1 carries a part of the human kappa light chain gene as a residue or tag. Twelve days after the date of transfection the cells were fixed and stained immunochemically using horseradish peroxidase-conjugated rabbit antibody to human kappa light chain (HRP-Rabbit anti-kappa) for the detection of cells containing ScAb. These cells give a positive response and are darker than the remaining cells; and FIG. 3 shows a histological section of muscle tissue sampled from a fish twelve days after intramusular injection of pCDNA3-BU1. The section was stained immunochemically using HRP-rabbit anti-kappa for the detection of ScAb. Several cells turned out positive (arrow heads) along the regenerating needle track (injection site) arrowed.

Gene Map

The following gene map is the DNA sequence of the construct comprising a single chain antibody gene (BU1) inserted into *E.coli* pCDNA3 plasmid (Invitrogen) used in the Example described below.

```
   1 cagtgtgcta acatgagggc agtgtgtttg atgctgactg ccttattgat 51 gctggaatat gtgtgccgga gtgaccaggt gcagctgcag gagtcaggac 101 ctggcctcgt gaaaccttct cagtctctgt ctctcacctg ctctgtcact 151 ggctactcca tcaccagtgg ttattactgg acctggatcc ggcagtttcc 201 aggaaataaa ctggaatgga tgggctacat aagctacgac ggtaccaata 251 actacaaccc atctctcaca aatcgaatct ccatcactcg tgacacatct 301 aagaaccagt ttttcctgaa gttgaaatct gtgactactg aggacacagc 351 tacatattac tgtgtaagag ggatctacta tggtaacgac tggtttgctt 401 actggggcca agggaccacg gtcaccgtct cctcagaagg caaatcttct 451 ggctctggct ctgaatctaa agtggatgac atcgagctca cccagtctcc 501 tgcctcccag tctgcatctc tgggagaaag tgtcaccatc acatgcctgg 551 caagtcagac cattggtaca tggttagcat ggtatcaaca gaaaccaggg 601 aaatctcctc agctcctgat ttatgctgca accagtttgg cagatggggt 651 cccatcaagg ttcagtggta gtggatctgg cacaaaattt tctttcaaga 701 tcagcagcct acaggctgaa gattttgtaa gttattactg tcaacaactt 751 tacagtactc cgtacacgtt cggaggggg accaagctcg agatcaaacg 801 gactgtggct gcaccatctg tcttcatctt cccgccatct gatgagcagt 851 tgaaatctgg aactgcctct gttgtgtgcc tgctgaataa cttctatccc 901 agagaggcca aagtacagtg gaaggtggat aacgccctcc aatcgggtaa 951 ctcccaggag agtgtcacag agcaggacag caaggacagc acctacagcc 1001 tcagcagcac cctgacgctg agcaaagcag actacgagaa acacaaagtc 1051 tacgcctgcg aagtcaccca tcagggcctg agttcgcccg tcacaaagag 1101 cttcaaccgc ggagagtcat aagttagata tccat (SEQ ID NO:1)
```

The BU1 insert (ScAb gene construct) is encoded by nucleotides 10 to 1125. The coding region nucleotides are 13 to 1122.

The above identified sequence can be found in the Genebank, the Accession Number is AF302092.

EXAMPLE

Single chain antibody genes were prepared according to the procedure described by McGregor et al; Spontaneous Assembly of Divalent Single Chain Antibody Fragments in *E-Coli*; Mol. Immunol. February 31 (3) pp 219 to 226; 1994. In short, the variable domains of the immunoglobulin H and L chain genes were cloned from hybridoma cell lines producing monoclonal antibodies to the fish pathogenic rhabdovirus viral haemorrhagic septicaemia virus (VHSV). The H and L chain variable domains were linked by a gene sequence encoding a 14 amino acid linker to generate a single chain antibody (ScAb) gene. As a tag to allow specific detection, the human kappa light chain constant domain gene was included at the 3' end of the gene. In order to ensure secretion of the ScAb polypeptides in eukaryotic cells, the nucleotide sequence encoding the 20 amino acid signal peptide of rainbow trout transforming growth factor beta (TGF-beta) was added at the 5' end of the gene.

The gene construct was inserted by blunt-end ligation into the eukaryotic expression vector pCDNA3 (Invitrogen) in the EcoR I site in the polylinker downstream of a cytomegalovirus (CMV) promoter (see FIG. 1). As a negative control in transfection experiments with cell cultures and immunoprotection trails in fish, the pCDNA3 plasmid without insert was used. Plasmid DNA was purified from overnight cultures of *E.coli* by use of commercial kits for anion-exchange chromatography as recommended by the supplier (Qiagen).

Other molecular biology procedures used were as followed by Sambrook et al in Molecular Cloning; A Laboratory Manual, Second Addition, Cold Spring Harbor Laboratory, USA, (1989). The variable domain genes from a hybridoma cell line secreting the VHSV-neutralising monoclonal antibody 3F1H10 were used. Cloning and sequencing of the variable domain genes has already been described. In the case of antibody 3F1H10, two amino acids substitutions were made to the H-chain (Asn35a to Thr and Lys64 to Thr). The ScAb carrying the variable domains of antibody 3F1H10 were called BU1.

Passaged fish cells designated (EPC) were transfected with an anionic transfection reagent (Superfect, Qiagen). Four to six days after transfection cell culture supernatant were harvested and analysed for antibody reactivity to VHSV. After removal of the supernatant, the cells remaining attached to the bottom of the cell culture wells were fixed in 80% cold acetone and stained by immuno-peroxidase using horseradish peroxidase-conjugated rabbit antibody to human kappa light chain (HRP-Rabbit anti-kappa) (DAKO, Denmark) in order to detect cells expressing ScAb. The effect of transfection on the susceptibility of the cell cultures to VHSV different doses of live VHSV was examined by adding the different doses to wells with cultures of transfected cells four days after transfection and the development of cytopathogenic effects (CPE) was recorded thereafter.

Injection of Plasmid DNA into Fish

Disease free rainbow trout fingerlings, average weight 4.5 g, were anaesthetised with 0.001% benzokaine and given two 25 μl injections of 20 μg plasmid DNA each, in the epaxial muscles below the dorsal fin. The fish were afterwards kept in groups of approximately 150 individuals in 120-liter tanks supplied with running tap water. The fish were fed ad libitum with commercial fish feed. Mean water temperature was 16° C. Injected plasmid constructs included the pCDNA3 vector without insert, and pCDNA3 carrying the ScAb BU1 gene construct (pCDNA-BU1) respectively.

Immunohistochemical Analysis for Expression of ScAb in Injected Fish

Twelve days after injection of plasmid DNA, 10 fish were sampled for each plasmid construct. After termination of the fish a section of muscle tissue was excised from the site of injection. The tissue was fixed in 10% phosphate buffered formalin and analysed by immunohistochemistry. Horseradish peroxidase-conjugated rabbit immunoglobulin (Ig) to human kappa light chain (HRP-rabbit anti kappa) (Dako, Denmark) was used for detection of expressed ScAb.

Sampling of Plasma from Fish

Blood samples were collected 12 days after injection of plasmid DNA from fish not exposed to VHSV. Due to the small size of the fish, sampling was performed with heparin-treated capillary tubes after cutting off the posterior fin of fully anaesthetised fish. The fish were terminated immediately afterwards. The blood samples were centrifuged at 5000 xg and plasma samples were collected and stored at −80° C. until analysed.

Serological Examination for VHSV-reactive ScAbs

Supernatant from transfected cell cultures and plasma samples from DNA-injected fish, were examined for anti-VHSV reactive ScAbs by a plaque-neutralisation (50% PNT) assay and by an enzyme-linked immunosorbent assay (ELISA).

The ELISA assay was performed in 96-well microtitre plates coated with purified VHSV. Bound ScAb's were detected with HRP-Rabbit anti-kappa. In order to demonstrate that the virus-neutralising activity detected in the trout plasma was due to the ScAbs produced by the fish and not by trout antibodies, two variants of the 50% PNT assay were also applied. One variant included parallel examination of the neutralising activity against the virulent VHSV3592B and a neutralisation resistant variant of VHS 3592B (VHSV DK-3542B) selected by cultivating virus in the presence of the neutralising Mab 3F1A2 which is highly similar to Mab 3F1H10. The other variant involved pre-incubation of the trout plasma with rabbit antibodies to human kappa light chain or with rabbit antibodies to trout immunoglobulin before incubation with virus. The 50% PNT microplate assay was performed as described by Olesen and Jørgensen in Detection of neutralising antibody to Egtved virus in rainbow trout by plaque neutralising with complement addition, J. Appl Ichthyol, Volume 2, pages 35 to 41.

Immunoprotection Trials in Fish

Eleven days after injection of the plasmid, groups of fish were exposed to (challenged with) the virulent VHSV DK-3592B isolate by immersion in water containing 100 000 50% tissue-culture infective doses per ml. Challenge was performed in 8-liter aquaria with 25-31 fish in each. Three replicate aquaria was included for each plasmid construct. Dead fish were afterwards daily recorded and collected. Dead fish from all tanks were analysed virologically for the presence of VHSV. Mean water temperature was 16° C. for the time of injection to immediately before challenge. At challenge, the fish ware adapted to a water temperature of 12° C. and this temperature was kept throughout the 20 day challenge period.

Immunochemcial Detection of Expressed ScAb in Cell Culture and in Fish

It was found that after immuno-peroxidase staining using the HRP-rabbit anti-human kappa, single cells expressing ScAb could be detected in EPC cell cultures transfected with the plasmid construct pCDNA3-BU1 (FIG. 2), whereas no positive cells were found in cultures transfected with pCDNA3 without insert. Similarly, expression of ScAb could be demonstrated in muscle sections from injected fish (FIG. 3). No positive cells were found in fish injected with pCDNA3 without insert.

Interference of ScAbs with Propagation of VHSV in Cell Culture

When monolayers of epithelial cell line of cap cell cultures were inoculated with VHSV four days after transfection, development of cytopathogenic effect (CPE) as a result of multiplication of VHSV was highly different in cultures transfected with pCDNA3 compared to cell cultures transfected with pCDNA3-BU1. In the latter case only certain plaques of cells became infected and died and there was no further development of CPE in the 8-day observation period. In contrast, when cultures transfected with pCDNA3 were inoculated, all cells became infected and were destroyed within 3-6 days as in a normal propagation of VHSV in EPC cells (Table 1).

TABLE 1

Susceptibility of transfected EPC cell cultures to VHSV

| Plasmid Construct used for Transfection | Cytopathogenic effect upon inoculation with VHSV* |
|---|---|
| pCDNA3 | Complete destruction of cell layer |
| pCDNA3-BU1 | Plaques |

*Concentrations of VHSV: $10^2$ – $10^3$ TCID-50/ml cell culture medium.

Detection of ScAbs to VHSV in the Fish

When the plasma from injected fish was analysed by ELISA for ScAbs recognising VHSV, a strong reaction was found in plasma from fish injected with pCDNA3-BU1. No reactivity was detected in plasma from fish injected with pCDNA3 without insert. As indicated in Table 2, the limited amounts of plasma available made it necessary to preform the analysis on pools of five individuals. The 50% PNT analysis was performed on individual plasma samples. All 10 individuals injected with pCDNA3-BU1 neutralised VHSV, whereas no neutralising activity was detected in plasma from fish injected with the pCDNA3 (Table 3).

When plasma from fish injected with pCDNA3-BU1 was preincubated with Rabbit anti-human kappa before testing in 50% PNT, the neutralising activity was eliminated, whereas no effect was observed upon pre-incubation with normal rabbit serum or with rabbit serum to trout Ig (Table 4). The neutralising activity of a positive trout serum control was unaffected by pre-incubation with normal rabbit serum and with rabbit anti-human kappa, but was highly reduced upon pre-incuabation with rabbit serum to trout Ig (Table 4). As with the parent monoclonal antibody 3F1H10, plasma samples from fish injected with pCDNA3-BU1 could neutralise the virulent VHSV DK-3592B isolate, but not a neutrailisation escape-mutant (not shown).

TABLE 2

Antibody reactivity in fish plasma: ELISA

| Fish No.* | Injected Plasmid | Reactivity with VHSF (A-496 mm) | |
|---|---|---|---|
| | | Dilution: 1/10 | Dilution: 1/80 |
| 36529 | pCDNA3 | 0 | 0 |
| 36686 | | 0 | 0 |
| 36844 | pCDNA3-BU1 | 3 | 1 |
| 16-20 | | 3 | 1 |

*The plasma samples were analysed in pools of 5 individuals.

TABLE 3

Antibody reactivity in fish plasma: Neutralisation of VHSV

| Fish No.* | Injected Plasmid | PNT-titres** |
|---|---|---|
| 36534 | pCDNA3 | <10 |
| 36849 | pCDNA3-BU1 | 160-640 |

*Plasma samples were analysed individually.
**Titres represent the reciprocal value of plasma dilutions reducing the number of plaques to approximately 50% compared to a control well without antibody/plasma.

TABLE 4

Effect of preincubation of trout plasma with rabbit antibodies on PNT-titres*

| | | PNT-titres | | |
|---|---|---|---|---|
| Fish No. | Injected Reagent | Normal rabbit | Rabbit to human chain kappa | Rabbit to trout Ig |
| 21-30 (1 pool) | pCDNA3-BU1 | 640 | <40 | 320-640 |
| Positive trout serum A7.1 | Killed VHSV | >10240 | >10240 | 320 |

*In order to allow detection of neutralising trout antibodies, trout complement was included as described above.

Infection Trial

When challenged with VHSV DK-3592B 11 days after injection of plasmid DNA, most of the fish injected with pCDNA3-BU1 survived whereas high mortalities were observed among fish injected with pCDNA3 (Table 5).

TABLE 5

Protection against VHSV

| Injected Plasmid | Accumulated mortality 20 days post challenge (mean of triplicate tanks) |
|---|---|
| pCDNA3 | 81% |
| pCDNA3-BU1 | 6% |

To our knowledge, this is the first report demonstrating establishment of protective immunity to an infectious pathogen in higher vertebrates by administration of genes encoding pathogen specific single chain FV antibodies. The protective activity of the pCDNA-BU1 construct fully correlated with the occurrence of neutralising anti-VHSV ScAbs in the plasma of injected fish, and although involvement of non-specific mechanisms cannot be completely excluded, it appear likely that the produced BU1 ScAb has been the major cause of protection following injection of the pCDNA3-BU1 plasmid DNA. Accordingly, in a later experiment including challenge of the fish with a virus isolate not recognised by the recombinant antibody fragment encoded by pCDNA-BU1, no protection was obtained.

In contrast to DNA-vaccines, including anti-idiotype vaccines, the administration of plasmid borne genes in this instance do not involve specific activation of the immune system in the individual. The principle is simply that single chain FV antibody polypeptides produced by the cells that take up the administered plasmid will be systemically distributed by the body fluids and protect the individual if infection with the pathogen occurs. This corresponds to the mechanism of prophylaxis against infectious diseases in humans through administration of antiserum or immunoglobulin from immunised donors or animals, but without side effects such as risk of concomitant transfer of infectious diseases or induction of hypersensitivity following repeated administrations. In order to avoid the pathogen variability overcoming the immunity established by the plasmid, practical use may involve administration of plasmids encoding genes of single chain variable fragments to several different epitopes of the pathogen or single chain FV antibody gene-expression library towards a given pathogen.

The principle of genetic immunoprophylaxis according to the invention can be extended to mammals and to humans in particular as it is a valuable tool for transient protection of individuals such as travelers against exposure to pathogens or toxins where no efficient vaccines are available. Similarly, the invention may be used for induction of the synthesis of antibodies of a desired specificity for use in immunodeficient individuals. Also the nucleic acid construct of the present invention could be used in individuals that produce an allergic response to certain allergens, such as pollen. In this connection, production or induction of antibody fragments to those allergens may be used for prevention of an allergic reaction.

Beside the prophylactic aspects of the invention, plasmid constructs carrying genes encoding pathogen/disease antigen specific single chain FV antibodies are of therapeutic use in certain diseases wherein the host immune system itself is unable to produce antibodies with the necessary activity.

The invention claimed is:

1. A plasmid for protection of a fish against viral haemorrhagic septicaemia virus (VHSV) comprising:
   a non-infectious DNA nucleic acid construct encoding a viral haemorrhagic septicaemia virus-neutralizing single chain antibody BU1 comprising (SEQ ID NO:1), operably linked to a secretion signal of transforming growth factor beta, a CMV promoter, and a polyadenylation signal.

2. A composition for passive immunization comprising the gene construct of claim 1 and a pharmaceutically acceptable diluent or carrier.

3. A method for prophylactically treating fish against viral haemorrhagic septicaemia virus comprising administering the plasmid of claim 1 to a fish via injection to the epaxial muscle below the dorsal fin of the fish.

* * * * *